United States Patent
Song et al.

(10) Patent No.: US 7,602,959 B2
(45) Date of Patent: Oct. 13, 2009

(54) VISUAL INSPECTION APPARATUS AND METHOD OF INSPECTING DISPLAY PANEL USING THE VISUAL INSPECTION APPARATUS

(75) Inventors: In-Cheol Song, Chungcheongnam-do (KR); Il-Ho Lee, Chungcheongnam-do (KR); Min-Young Won, Gyeonggi-do (KR); Chan-Hyang Lim, Gyeonggi-do (KR)

(73) Assignee: Samsung Electronics Co, Ltd., Suwon-Si (KR)

( * ) Notice: Subject to any disclaimer, the term of this patent is extended or adjusted under 35 U.S.C. 154(b) by 700 days.

(21) Appl. No.: 11/367,138

(22) Filed: Mar. 3, 2006

(65) Prior Publication Data

US 2006/0215898 A1    Sep. 28, 2006

(30) Foreign Application Priority Data

Mar. 23, 2005    (KR) ...................... 10-2005-0024115

(51) Int. Cl.
    *G06K 9/00*    (2006.01)
(52) U.S. Cl. ........................ 382/141; 382/148; 382/151
(58) Field of Classification Search ................. 382/141, 382/148, 151
    See application file for complete search history.

(56) References Cited

U.S. PATENT DOCUMENTS 5,036,385 A * 7/1991 Eichenlaub .................. 348/59
2005/0018897 A1 * 1/2005 Choi et al. .................. 382/141

* cited by examiner

*Primary Examiner*—Matthew C Bella
*Assistant Examiner*—Mike Rahmjoo
(74) *Attorney, Agent, or Firm*—F. Chau & Associates, LLC

(57) ABSTRACT

A visual inspection apparatus includes a plurality of cameras for photographing a display panel and a processor for processing the photographed image. Specifically, the visual inspection apparatus includes: a work table having a panel mounting unit on which a display panel is mounted; a camera module which is disposed in a direction normal to the panel mounting unit and which has a plurality of cameras arranged in a matrix; and a processor for processing the images of the display panel photographed with the cameras. The plurality of cameras is arranged in a matrix with variable distances between the cameras. Since the visual inspection apparatus includes the cameras arranged in a matrix, it can be used to effectively detect a variety of defects.

9 Claims, 14 Drawing Sheets

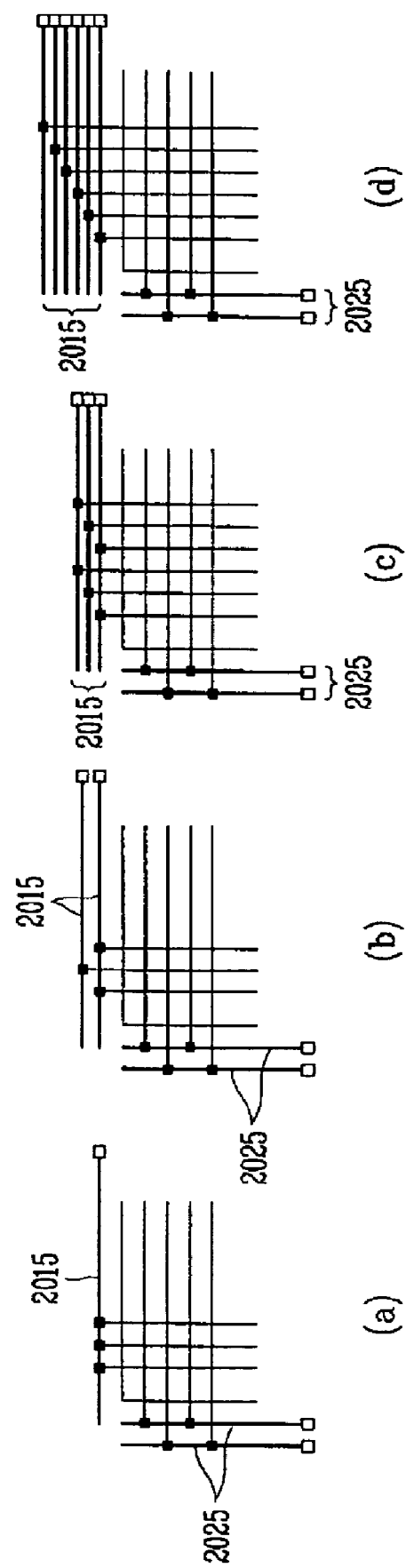

VISUAL INSPECTION APPARATUS AND METHOD OF INSPECTING DISPLAY PANEL USING THE VISUAL INSPECTION APPARATUS

This application claims priority to Korean Patent Application No. 2005-0024115, filed on Mar. 23, 2005, and all the benefits accruing therefrom under 35 U.S.C. §119, and the contents of which in its entirety are herein incorporated by reference.

BACKGROUND OF THE INVENTION (a) Field of the Invention

The present invention relates to a visual inspection apparatus and a method of inspecting a display panel using the visual inspection apparatus.

(b) Description of the Related Art

Flat panel displays (FPD) such as liquid crystal displays, organic light emitting displays, field emission displays (FED), and plasma display panels (PDP) have been developed and are widely used.

Such flat panel displays (FPD) should be subjected to various inspection processes before coming to the market. A variety of defects in a display panel such as short-circuits between lines and particle contamination may occur while manufacturing the same. Accordingly, it is very important in view of manufacturing yield to detect such defects, to repair or discard the defective panels, and to remove causes of the defects.

Among a variety of inspections, a visual inspection for detecting defective pixels and defective lines by the use of an image displayed on the display panel is often used. In the visual inspection, the defects are detected by the use of a visual inspection apparatus or the naked eye of a person. The visual inspection is generally performed when an image can be displayed on the display panel with application of image signals, that is, after the individual panels are manufactured, in the processes of manufacturing a display panel.

During such inspection, an error that a defective display panel is determined to be a normal display panel or a normal display panel is determined to be a defective display panel may occur. If much time is required for the inspection, the overall manufacturing time for one product increases, and the size of the display panel may be different for different products. Accordingly, when various groups of products are manufactured, the inspection process should be optimized for every group of products. As a result, inspection accuracy, high inspection speed, and easy modification of inspection conditions are very important aspects when inspecting a display panel.

Therefore, an inspection apparatus that can perform an inspection process at higher speed, accurately detect defects, and cope with various groups of products is required.

SUMMARY OF THE INVENTION

It is an object of the present invention to provide a visual inspection apparatus with improved inspection capability, and a method of inspecting a display panel using the visual inspection apparatus.

A visual inspection apparatus according to the present invention includes a plurality of cameras for photographing a display panel, and a processor for processing the photographed image.

Specifically, according to an aspect of the present invention, the visual inspection apparatus includes a work table having a panel mounting unit on which a display panel is mounted, a camera module which is disposed in a direction normal to the panel mounting unit and which has a plurality of cameras arranged in a matrix, and a processor for processing the images of the display panel photographed with the cameras. The plurality of cameras is arranged in a matrix with variable distances between the cameras.

The visual inspection apparatus may further include a first light source for supplying light from the bottom side of the work table to the panel mounting unit, and a second light source for supplying light from the top side of the work table to the panel mounting unit.

The visual inspection apparatus may further include an optical sheet which is disposed between the first light source and the panel mounting unit, and to which a distance from the panel mounting unit is variable.

A method of inspecting a display panel according to the present invention includes photographing a display panel with a plurality of cameras, and processing the photographed images by the use of a processor.

Specifically, according to another aspect of the present invention, the method of inspecting a display panel includes mounting a display panel on a panel mounting unit, photographing the display panel with a plurality of cameras arranged in a matrix, and processing the images of the display panel that are photographed with the cameras, with the use of a processor.

BRIEF DESCRIPTION OF THE DRAWINGS

The above and other features and advantages of the present invention will become more apparent by describing in detail exemplary embodiments thereof with reference to the attached drawings, in which:

FIGS. 5A and 5B are diagrams illustrating a panel and inspection pads and inspection lines formed on the panel;

DETAILED DESCRIPTION OF THE EMBODIMENTS

Hereinafter, exemplary embodiments of the present invention will be described in detail with reference to the accompanying drawings.

Figure 1:
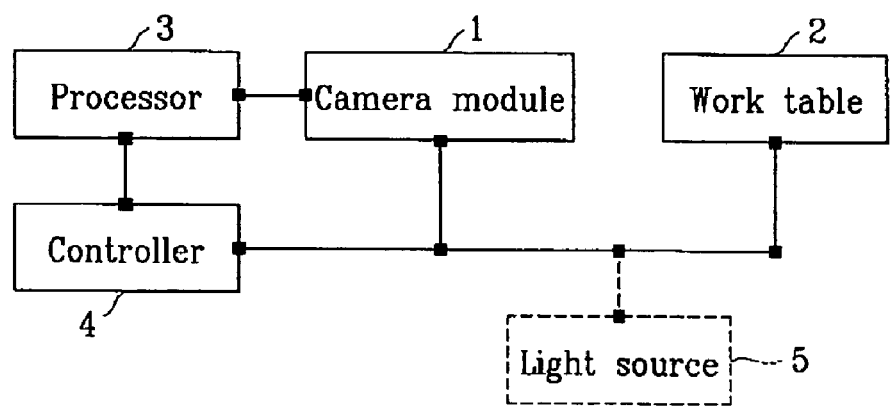
FIG. 1 is a diagram illustrating relationships between elements of a visual inspection apparatus according to an embodiment of the present invention.

FIG. 1 is a diagram illustrating relationships between elements of a visual inspection apparatus according to an embodiment of the present invention.

Referring to FIG. 1, the visual inspection apparatus includes a camera module 1, a work table 2, a processor 3, and a controller 4. The visual inspection apparatus may further include a light source 5 as needed.

According to an embodiment of the present invention, the controller 4 controls the camera module 1, the work table 2, and the light source 5 in accordance with signals from the processor 3. Generally, the controller 4 can control a distance between the camera module 1 and the work table 2 or a distance between cameras (not shown) fitted into the camera module 1, and control focuses and magnifications of the cameras. In addition, the controller 4 can control vibration of the work table 2, and attachment and detachment of a display panel (not shown). Furthermore, the controller 4 can control On/Off and brightness of the light source 5.

According to an embodiment of the present invention, the processor 3 can examine the photographing areas overlapped by the respective cameras, or determine existence of a defect or kinds of defects in the photographed image of the display panel. The processor 3 can determine a coordinate of a defect in the photographed image of the display panel, or can generate image data on the entire display panel. Furthermore, the processor 3 can transmit such data to other devices requiring the data, such as a device (not shown) for repairing the detected defect.

Figure 2:
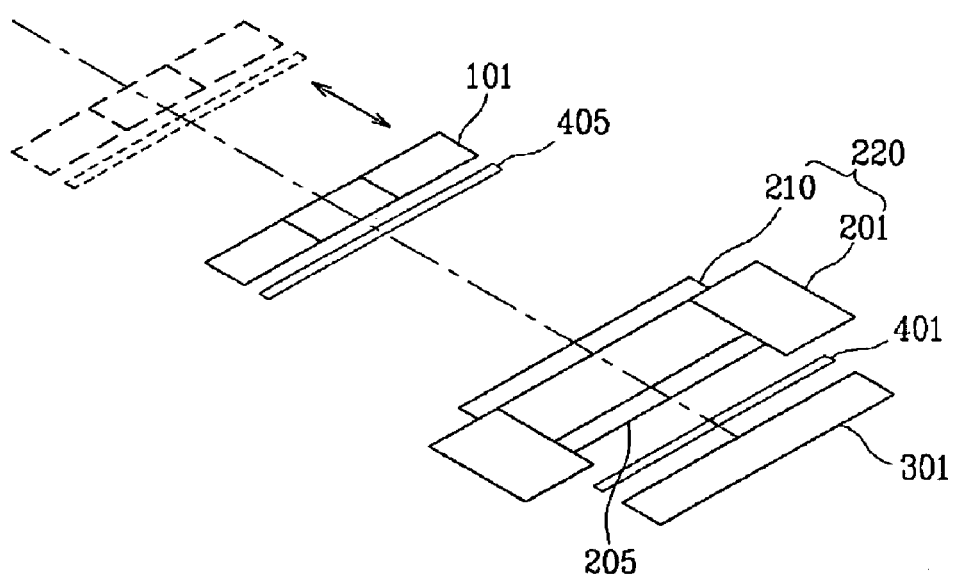
FIG. 2 is a diagram illustrating positional relationships between a camera module, a work table, and a light source.

FIG. 2 is a diagram illustrating positional relationships between a camera module, a work table, and a light source.

Referring to FIG. 2, a camera module 101 is disposed in a direction normal to a work table 220, and a light source 301 is disposed below the work table 220.

The camera module 101 includes a plurality of cameras (not shown), and is disposed so as to vertically photograph a display panel (not shown) mounted on the work table 220. The plurality of cameras can be arranged in a matrix. In order to obtain a desired image, a distance between the camera module 101 and the work table 220 can be adjusted.

The work table 220 includes a supporting member 201 and a panel mounting unit 210. The panel mounting unit 210 has a display panel mounted thereon, and has a signal supply unit (not shown) for supplying an image signal to the mounted display panel.

The light source 301 is used to display an image on a display that does not emit light, such as a liquid crystal display. If necessary, an optical sheet 205 may be interposed between the light source 301 and the panel mounting unit 210.

A distance between the panel mounting unit 210 and the optical sheet 205 can be changed. This is because dust or the like attached to the top or bottom of the optical sheet 205 can affect the image of the display panel. For example, when the optical sheet 205 to which dust is attached is disposed directly below the display panel mounted on the panel mounting unit 210, the dust can hinder the passage of light and the portion having the dust can be dark. The optical film 205 may be a diffusion film.

If necessary, the visual inspection apparatus may further include a lower polarizing film 401 disposed between the light source 301 and the panel mounting unit 210, and an upper polarizing film 405 disposed between the panel mounting unit 210 and the camera module 101. The polarizing films 401 and 405 are required for displaying an image on a display such as a liquid crystal display. The upper polarizing film 405 may be used in a display that emits light.

The work table 220 is tilted by an angle between 0 degrees and 60 degrees from a horizontal plane. The camera module 101 disposed in the normal direction to the work table 220 is tilted by the same angle as the work table 220 so as to vertically photograph the display panel mounted on the panel mounting unit 210 of the work table 220. Such a tilt allows an operator to easily observe the display panel mounted on the work table 220.

For example, a visual inspection apparatus for inspecting a liquid crystal display panel according to an embodiment of the present invention may include a light source 301, a lower polarizing film 401, an optical sheet 205, a panel mounting unit 210 disposed on a work table 220, an upper polarizing film 405, and a camera module 101. The positions of the lower polarizing film 401 and the optical sheet 205 with respect to a path of light emitted from the light source 301 can be changed.

A visual inspection apparatus for inspecting a display panel that emits light according to an embodiment of the present invention may include a panel mounting unit 210 disposed on a work table 220, and a camera module 101. If necessary, the visual inspection apparatus may further include an upper polarizing film 405.

Figure 3A:
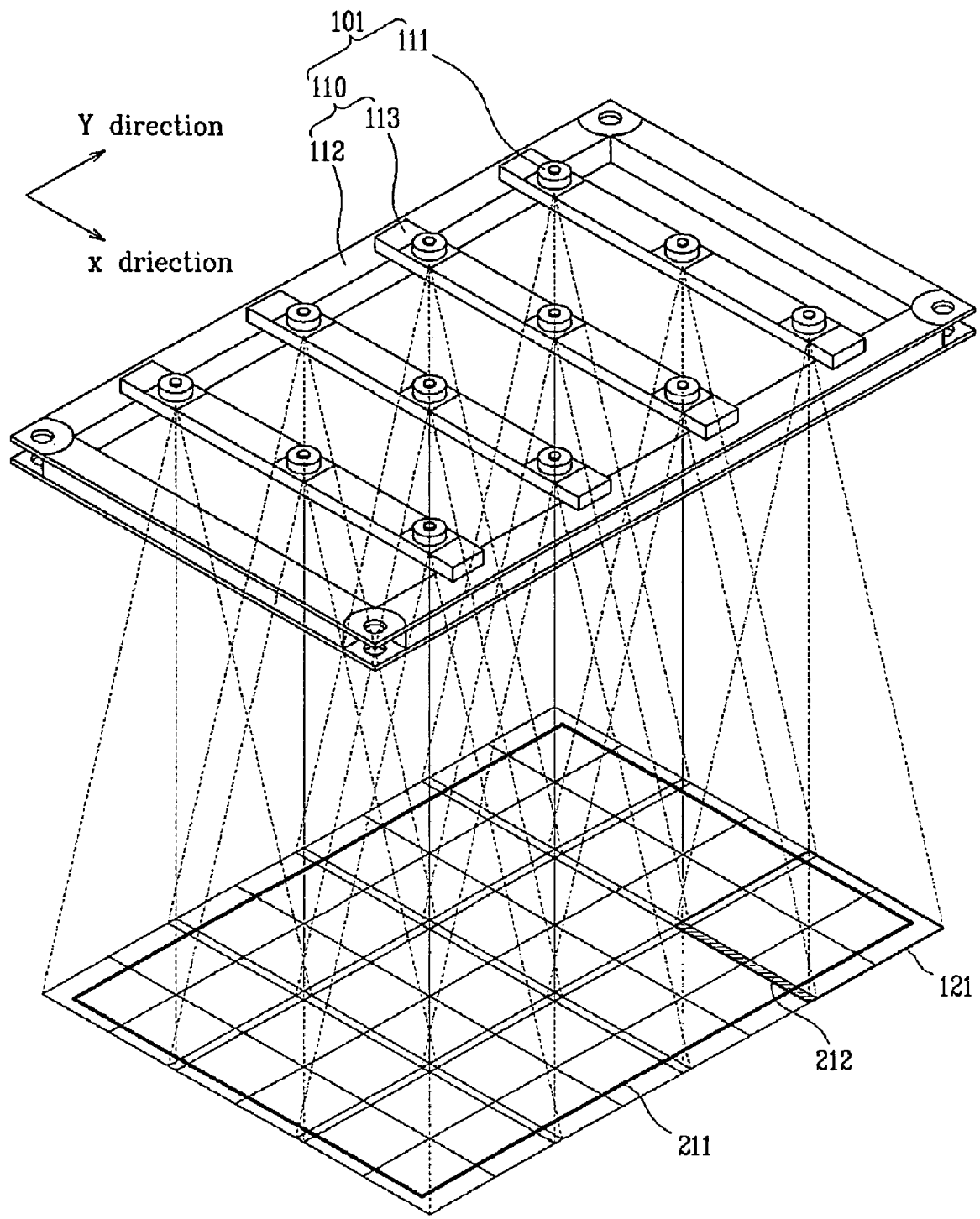
FIGS. 3A to 3C are diagrams illustrating a camera module and an image pickup area of a visual inspection apparatus.
Figure 3B:
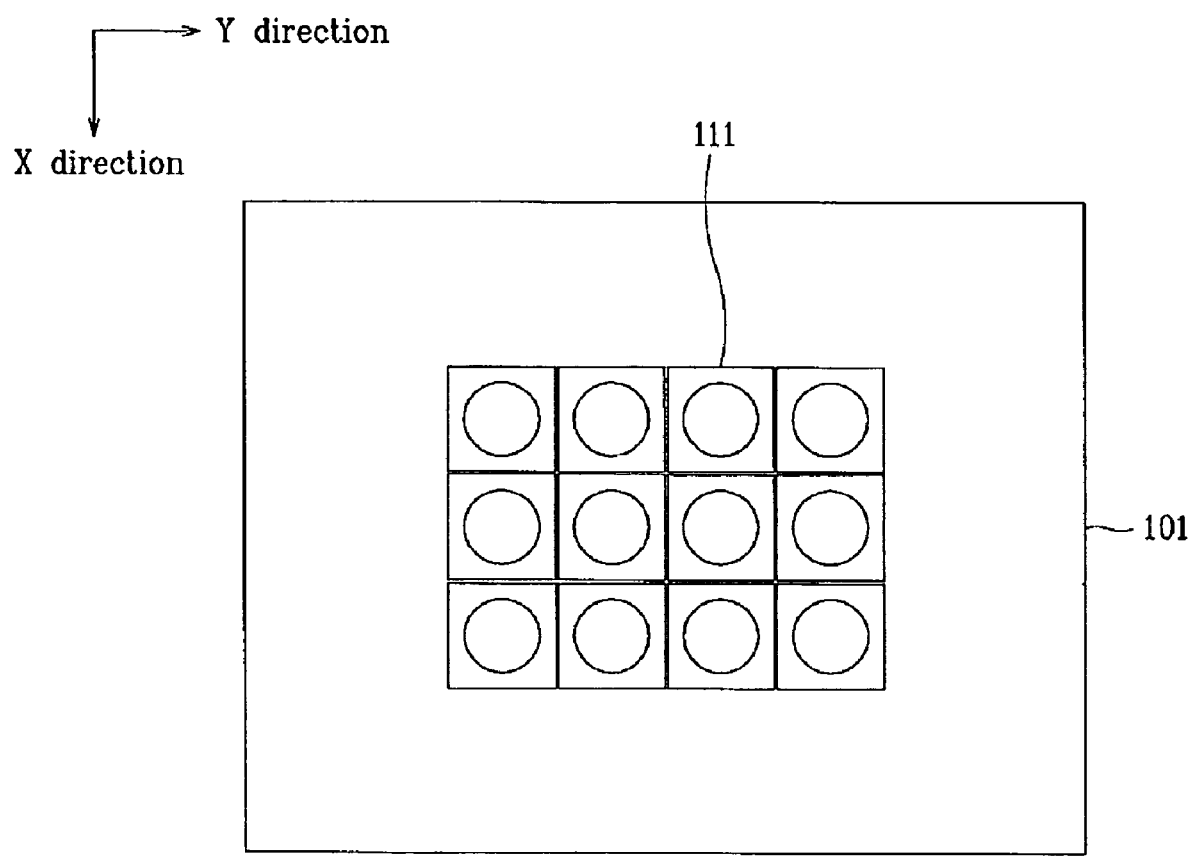
Figure 3C:
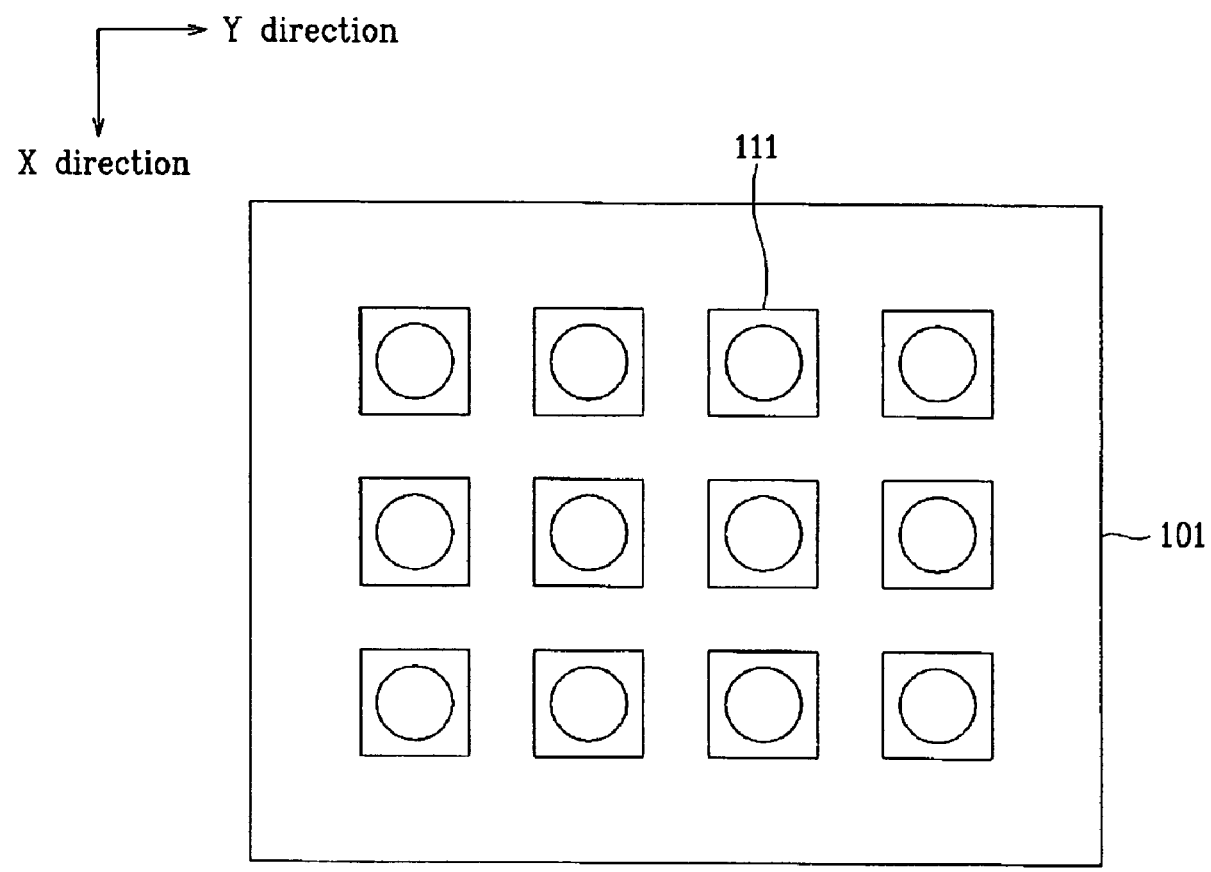

FIGS. 3A to 3C are diagrams illustrating the camera module and the photographing area in the visual inspection apparatus.

Referring to FIG. 3A, the camera module 101 includes a plurality of cameras 111 and a camera mounting unit 110 on which the cameras are mounted. The camera mounting unit 110 includes a rectangular frame 112 and a plurality of horizontal supports 113 that are connected in parallel to cross the rectangular frame 112. The cameras 111 are mounted on the horizontal supports 113 in lines to form a matrix. The number of cameras 111 disposed along the horizontal support 113, that is, in the X direction, and the number of cameras 111 disposed in the Y direction perpendicular to the X direction are not particularly limited, but it is sufficient if the distances between the cameras 111 or the distance to a display panel 211 can be adjusted to photograph the entire display panels 211 of various sizes.

The cameras 111 photograph the display panel 211 at specific partitioned areas, and the photograph areas 121 photographed with the cameras 111 can overlap with each other. The overlapped photograph areas are denoted by reference numeral 212. The entire display panel 211 and the outer edges thereof are all photographed with the cameras 111. A reference panel having the same size is photographed in advance using the cameras 111, and the processor then examines the overlapped photographed areas 212 on the basis of the photographed images of the reference panel. In one embodiment, the reference panel displays repeated specific patterns (such as dots, lines, and figures), and the image of a display panel 211 and the image of the reference panel are compared with each other on the basis of distances between the patterns measured with the cameras 111 or the specific pattern and a specific point on the reference panel.

The positions of the cameras arranged in a matrix can be changed to alter conditions of the camera module 101 so as to correspond to display panels having various sizes and a variety of types of defects.

FIGS. 3B and 3C are diagrams illustrating the cameras 111 of the camera module 101 before and after movement of the cameras 111. FIG. 3B shows a case in which the cameras 111 are gathered close to each other and FIG. 3C shows a case in which the cameras 111 are set further apart from each other. The distances between the cameras 111 in the camera module 101 can be changed. The horizontal distances and the vertical distances may have different fixed widths, or they may be the same. In this way, by changing the distances between the cameras 111, it is possible to effectively cope with display panels 211 having various sizes and a variety of photographing magnifications.

Figure 4:
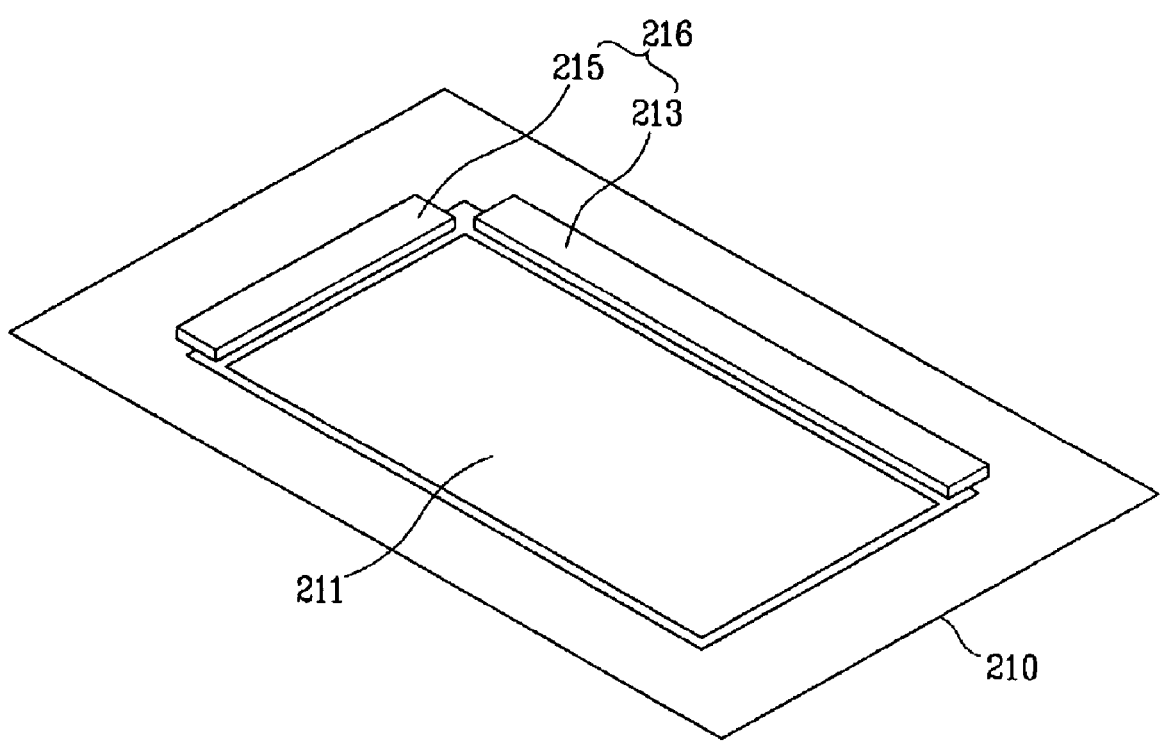
FIG. 4 is a diagram illustrating a panel mounting unit.

FIG. 4 is a diagram illustrating the panel mounting unit.

Referring to FIG. 4, the panel mounting unit 210 is used to mount a display panel 211 on the unit 210 and a signal supply unit 216 is used to supply image signals to the mounted display panel 211. The signal supply unit 216 has an arrangement and shape corresponding to the kind of the display panel 211 and the arrangement of inspection pads (not shown) disposed on the display panel 211. For example, when the display panel 211 has inspection pads for data signals at one side thereof and inspection pads for gate signals at the other side, the signal supply unit 216 has a data signal supply section 213 at a position corresponding to the one side and a gate signal supply section 215 at a position corresponding to the other side. As an alternative, when the display panel 211 has inspection pads for data signals and inspection pads for gate signals together at one side thereof, the signal supply unit 216 is also disposed at the position corresponding to the one side. That is, the signal supply unit 216 is disposed at the position corresponding to the inspection pads supplied with image signals for displaying an image on the display panel 211.

Figure 5A:
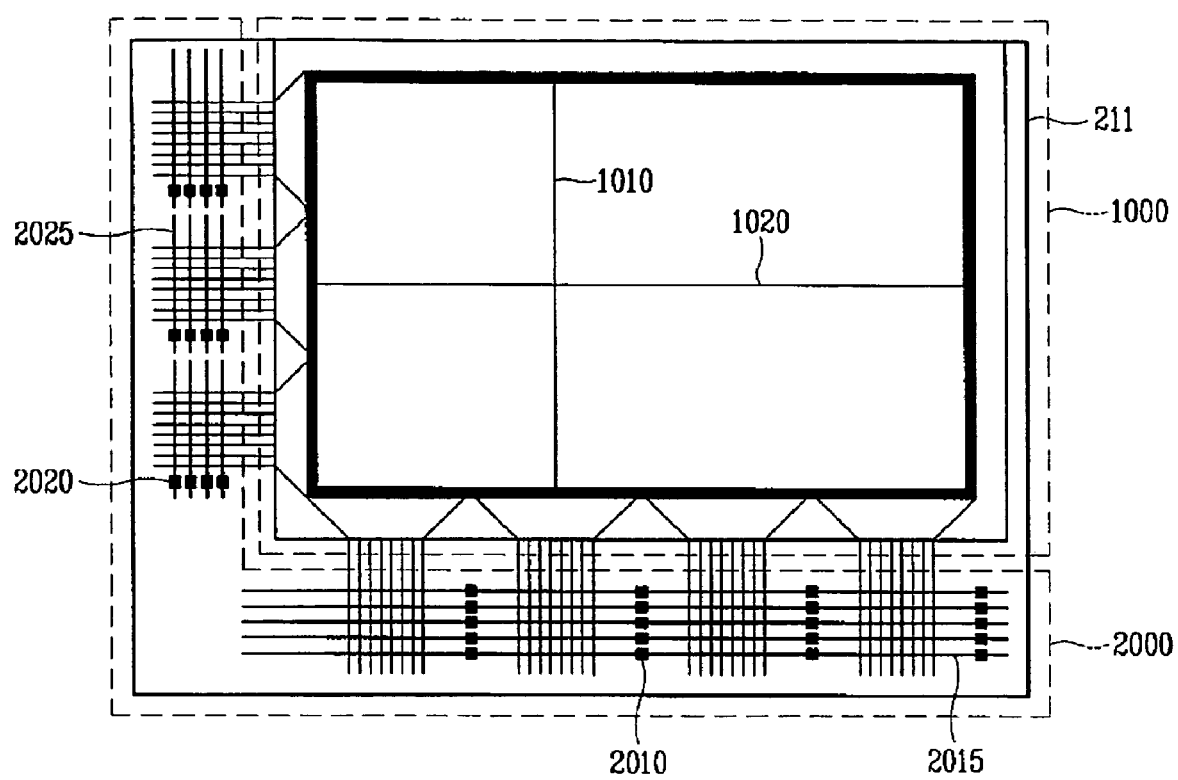

FIGS. 5A and 5B are diagrams illustrating a display panel and inspection pads and inspection lines formed on the display panel.

FIG. 5A is a diagram illustrating a display panel in which image signal lines 1010 and 1020 are intersected in a matrix shape.

Referring to FIG. 5A, the display panel 211 is divided into a display area 1000 for displaying an image and a peripheral area 2000 thereof. A plurality of signal lines 1010 and 1020 orthogonally intersecting each other exist in the display area 1000. That is, in the display area 1000, a plurality of first signal lines 1010 are disposed parallel to each other (not shown) and a plurality of second signal lines 1020 are disposed parallel to each other. Generally, active elements are disposed in the vicinity of intersections between the signal lines. The signal lines 1010 and 1020 extend to the peripheral area 2000, and circuits for supplying image signals are electrically connected to the signal lines 1010 and 1020 disposed in the peripheral area 2000. The circuits are built in the display panel 211 or are electrically connected to the image signal lines in the form of chip.

In order to inspect the display panel 211 while it is being manufactured, the signal lines 1010 and 1020 are selectively connected to inspection lines 2015 and 2025 in the peripheral area 2000. The signal supply unit (which is denoted by reference numeral 216 in FIG. 4) of the panel mounting unit (which is denoted by reference numeral 210 in FIG. 4) can supply image signals to the display panel 211 through inspection pads 2010 and 2020 that are electrically connected to the inspection lines 2015 and 2025.

The inspection pads 2010 and 2020 and the inspection lines 2015 and 2025 can be variously designed, depending upon inspection purposes thereof. For example, in FIG. 5A, the inspection lines 2015 for first signals are selectively connected to all of the first signal lines 1010, but the inspection lines 2025 for second signals are selectively connected to some of the second signal lines 1020. The inspection pads 2010 for the first signals may be disposed between the inspection lines 2015 in consideration of delay of signals or the like. The position and arrangement of the signal supply unit (which is denoted by reference numeral 216 in FIG. 4) of the panel mounting unit (which is denoted by reference numeral 210 in FIG. 4) is determined to correspond to the positions and arrangement of the inspection pads 2010 and 2020. On the other hand, FIG. 5B shows a various number of inspection lines 2015 and 2025 and selective connections to the image signal lines in various examples of the inspection lines 2015 and 2025 in a display panel.

Generally, the inspection lines including the inspection pads are removed during manufacture of a display panel after inspection, and the removal of the inspection lines is performed by using either or both of a laser cutting method and a grinding method using a grinder.

Figure 6:
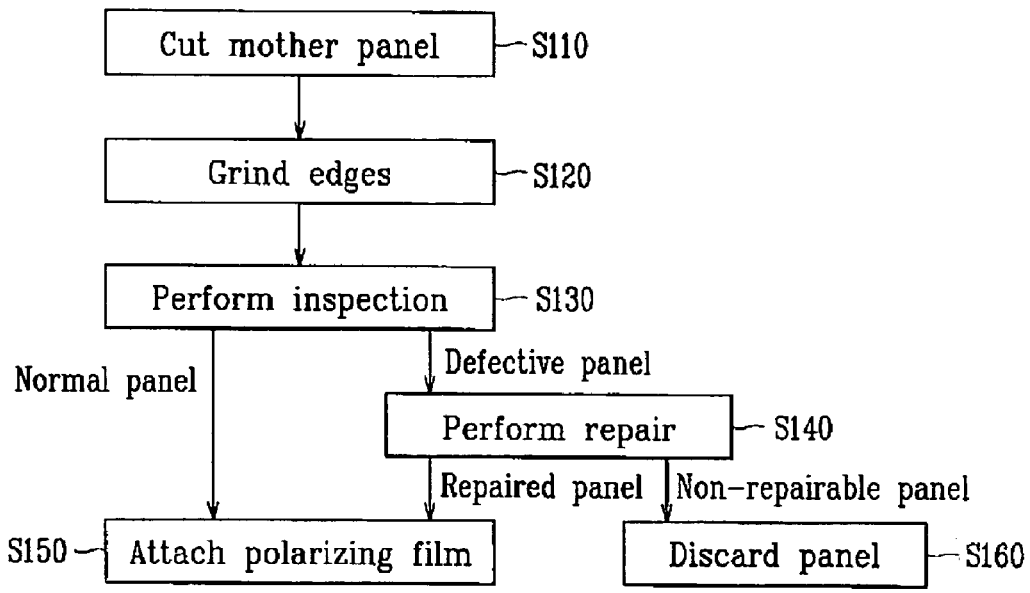
FIG. 6 is a flowchart illustrating a part of a method of manufacturing a panel.

FIG. 6 is a flowchart illustrating a part of a method of manufacturing a display panel.

Referring to FIG. 6, a mother panel to which upper and lower panels are attached is cut into a plurality of display panels (S110). Micro-cracks are removed by grinding the edges of the cut display panels (S120). Next, a display panel inspection process is performed with the use of the inspection apparatus of the present invention (S130). At this time, a repairing process is performed to any defective panels (S140). Polarizing films are attached to non-defective display panels and display panels having been subjected to the repairing process to manufacture display panels (S150), and non-repairable display panels are abandoned (S160).

The display panel inspection process (S130) is performed through the use of visual inspection or photographic inspection, or both. The photographic inspection can be performed with the use of the visual inspection apparatus according to the present invention. When the visual inspection apparatus according to the present invention is used, the display panel inspection process may be performed with the use of the inspection apparatus independently, or it may be performed in an in-line course combined with other processes. In order to sequentially inspect a plurality of display panels, the inspection and movement of the display panels in the visual inspection apparatus may be continuous. That is, a plurality of display panels may be sequentially inspected and moved through the steps of mounting a display panel on the panel mounting unit of the work table, photographing the display panel with a plurality of cameras arranged in a matrix, detaching the photographed display panel from the panel mounting unit, and then mounting another display panel on the panel display unit. The check for defects is performed by processing the photographed images of the display panels.

Such an in-line inspection process or such a continuous and sequential inspection process can enhance the inspection speed of the display panels.

Figure 7:
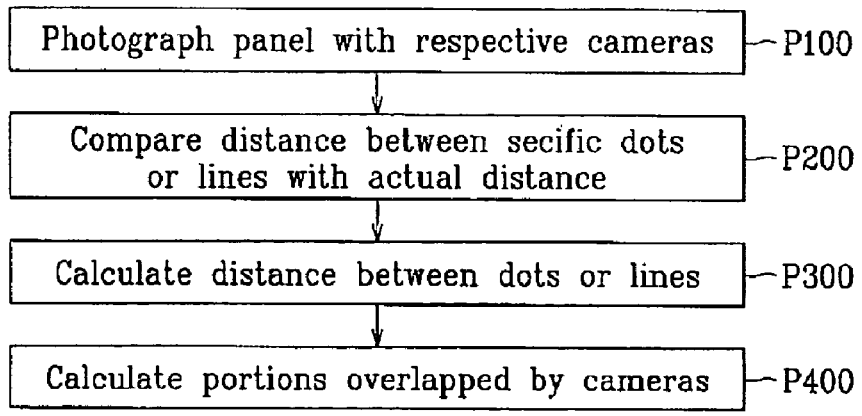
FIG. 7 is a flowchart illustrating a pre-processing operation for processing an image in the visual inspection apparatus.

FIG. 7 is a flowchart illustrating a pre-processing operation for processing an image in the visual inspection apparatus.

In order to photograph a display panel mounted on the panel mounting unit and process the image of the display panel, it is necessary to check the overlapping areas of the images photographed with the cameras. Generally, the overlapping areas should be distinguished by comparing the images photographed with the cameras with a preset size of the display panel. Accordingly, patterns which are regularly repeated are displayed on the display panel and the display panel is photographed with the cameras (P100). The processor recognizes the patterns photographed with the cameras and compares the distances between the patterns in the images photographed with the cameras or the distance from a specific position to a specific pattern in the display panel with the distance in the actual display panel (P300), thereby checking the overlapping areas in the images photographed with the cameras (P400).

An example of the patterns which are regularly repeated may be dot patterns or line patterns. Accordingly, the cameras photograph the dot patterns or the line patterns (P100) and the processor recognizes the patterns (P200), compares the distances with the actual distances (P300), and calculates the overlapping areas by the cameras (P400).

Figure 8A:
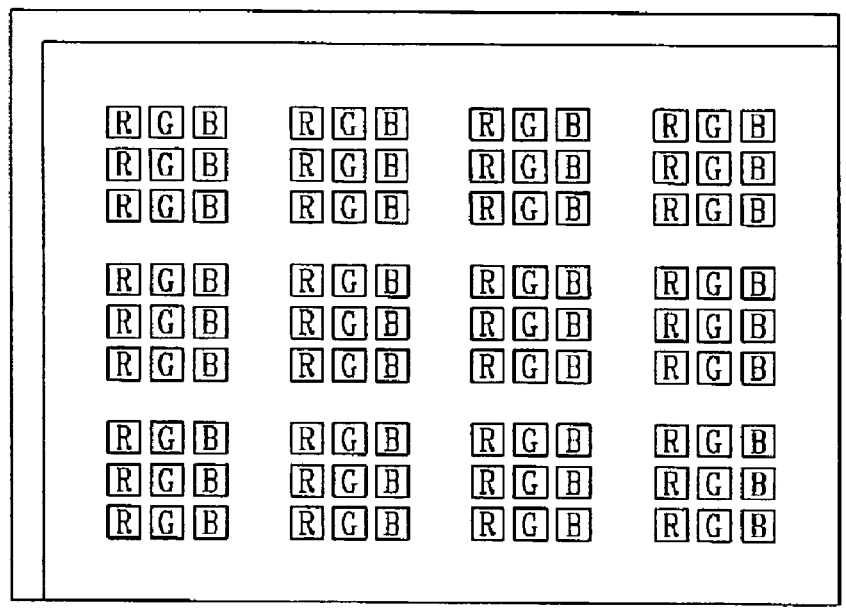
FIGS. 8A and 8B are diagrams illustrating an image of a display panel used for the pre-processing operation shown in FIG. 7.
Figure 8B:
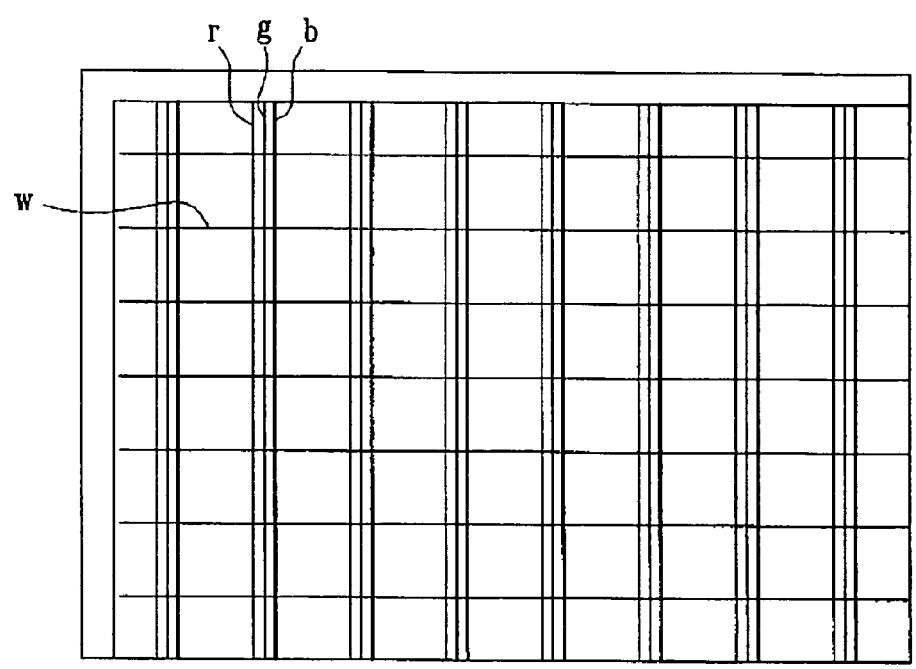

FIGS. 8A and 8B are diagrams illustrating an image of a display panel used for the pre-processing operation shown in FIG. 7.

FIG. 8A is a diagram illustrating the dot patterns which are regularly repeated, where a red dot R, a green dot G, and a blue dot B are repeatedly arranged in the horizontal direction at a constant interval. FIG. 8B is a diagram illustrating the line patterns which are regularly repeated, where a red line r, a green line g, and a blue line b extending in the vertical direction are repeatedly arranged in the horizontal direction at a constant interval and a white line w is repeatedly arranged in the vertical direction. The dot patterns or the line patterns may be displayed with different colors or with a uniform color. On the other hand, the patterns may be displayed with a specific shape or in combination with different patterns, if necessary.

Figure 9:
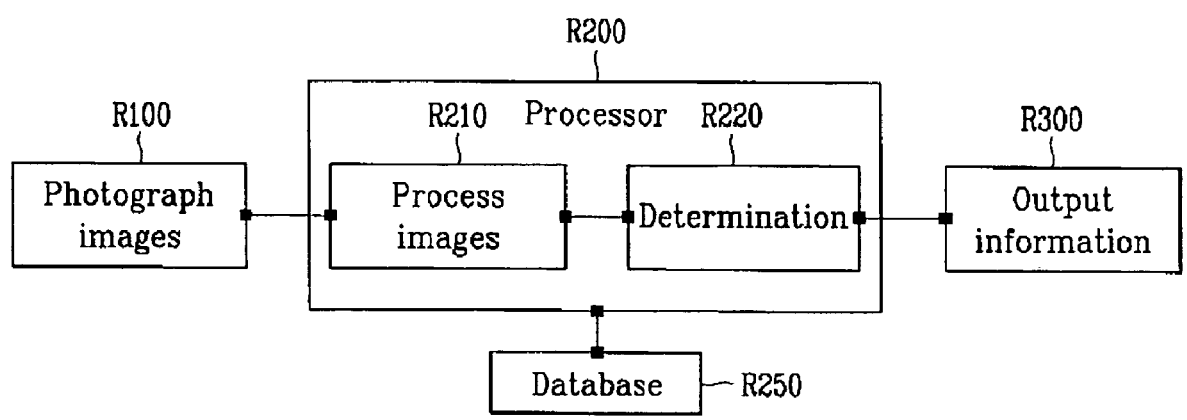
FIG. 9 is a diagram illustrating a method of detecting a defective panel by the use of the visual inspection apparatus.

FIG. 9 is a diagram illustrating a method of detecting a defective panel by the use of the visual inspection apparatus.

The images R100 photographed with the cameras are sent to the processor R200, and are subjected to an image processing operation R210 and a determination operation R220. In the operations, the overlapping portions of the images photographed with the cameras are calculated and existence of any defects is determined. When differences between the irregular portions of the photographed images and the normal portions exceed an allowable error range, the portions are determined as defects. For example, when the display panel displays black and pixels or lines displaying white exist, or when the display panel displays white and pixels or lines displaying black exist, the defects are determined on the basis of differences from the peripheral images. In order to determine the overlapping portions or the defects of the photographed images, the processor utilizes information recorded in a database R250 and stores necessary information in the database R250. On the other hand, the processor sends determination data and information on the processed images to other units or outputs them by the use of a display unit (R300).

For example, brightness intensities of the photographed images are expressed in coordinates by assigning value corresponding to brightness intensities. At this time, the brightness may be continuously measured or it may be measured at intervals corresponding to each pixel. The measured brightness data are interpolated and the brightness pattern thereof is determined, thereby determining irregular portions of the data. Next, on the basis of whether differences in intensity between the irregular portions and the normal portions exceed the allowable error range, the presence of defects in the display panel and the defective portions are determined.

On the other hand, when a factor indicating a difference in intensity between the defective portions and the normal portions exists in addition to the brightness, the intensity of the photographed images can be expressed in coordinates on the basis of the factor, thereby determining the presence of defects. Such a factor can include brightness, saturation, color, and combinations thereof.

Figure 10A:
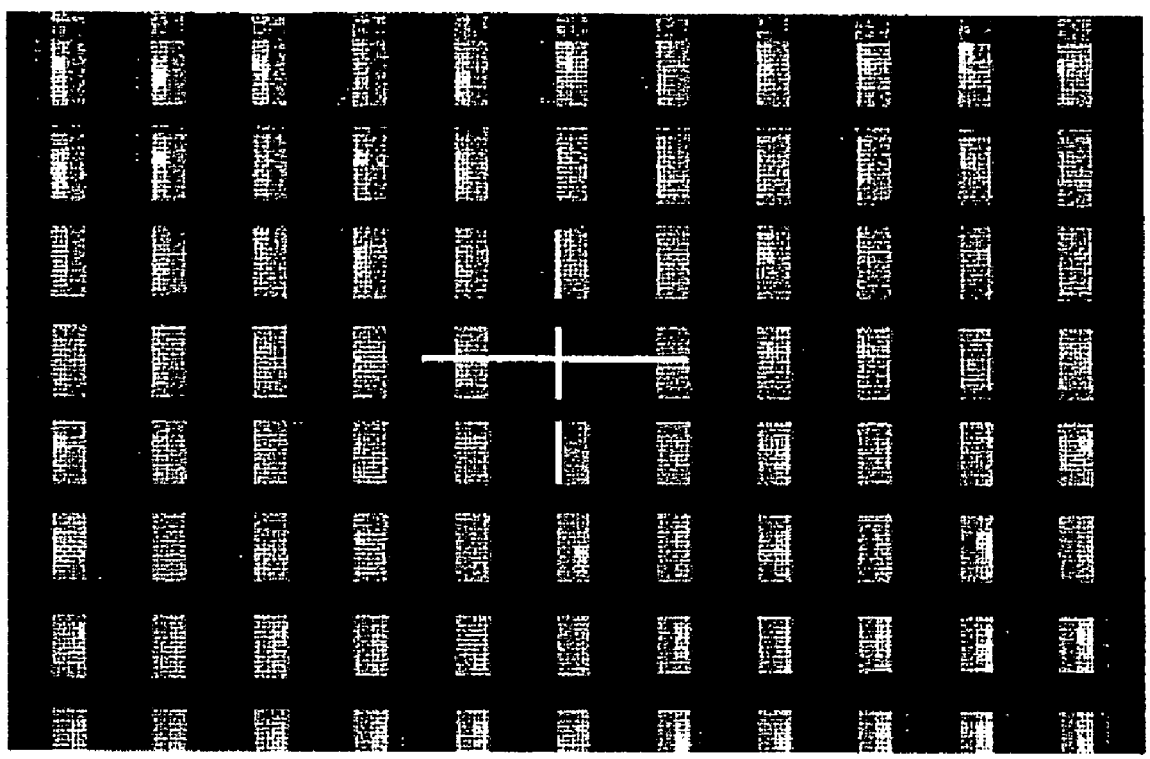
FIGS. 10A and 10B are photographs obtained by photographing a defective panel by the use of the visual inspection apparatus.
Figure 10B:
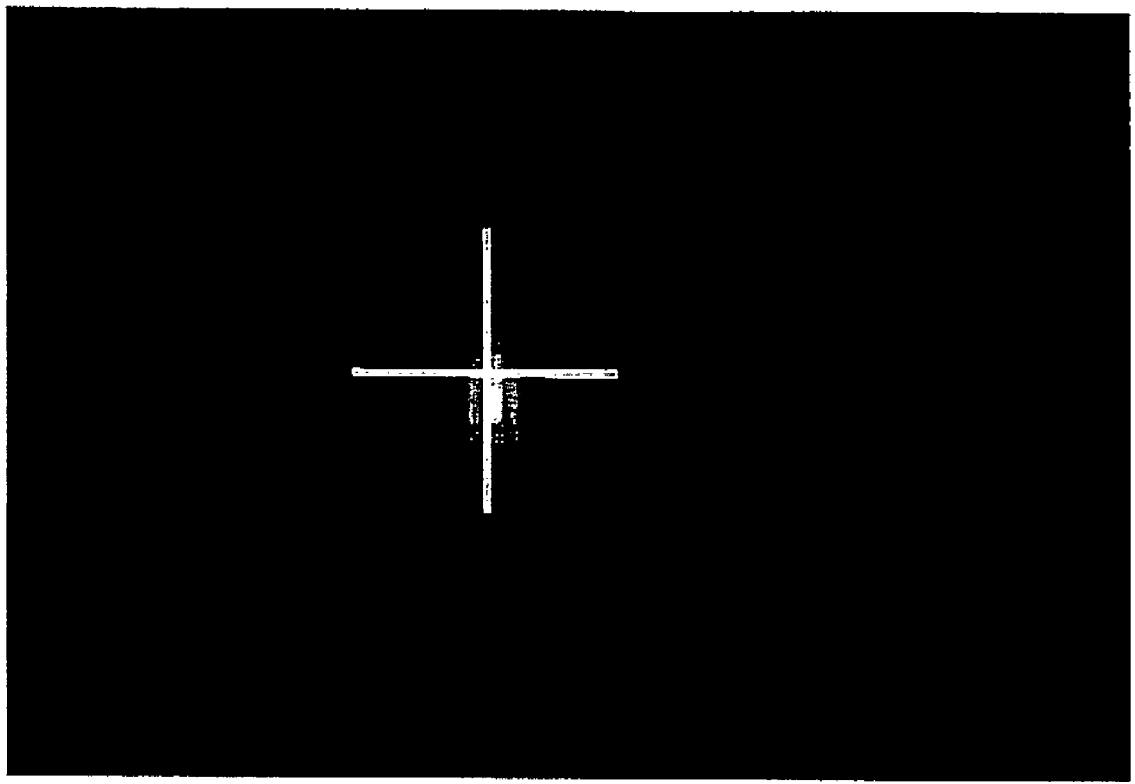

FIGS. 10A and 10B are photographs obtained by photographing a defective panel with the use of the visual inspection apparatus.

Referring to FIGS. 10A and 10B, a pixel defect is detected in the vicinity of the center of a "+" shape. That is, the existence of a defect and the defect position are detected on the basis of the difference in intensity between the normal portion and the irregular portion. In addition, a line defect or a surface stain may be detected.

Figure 11:
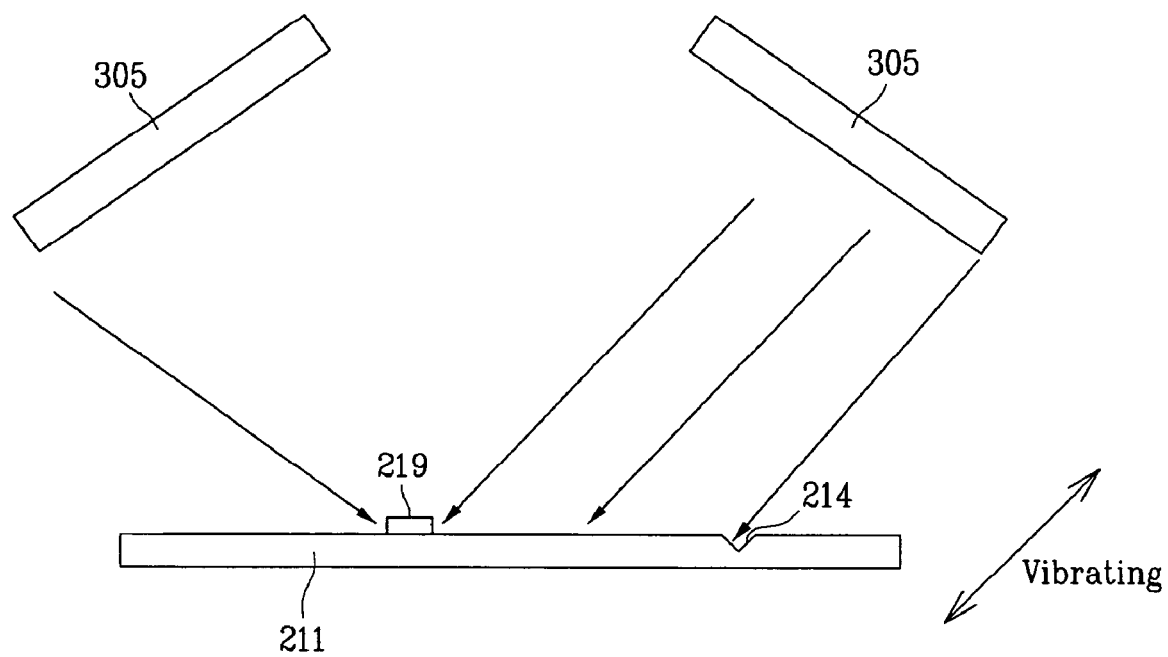
FIG. 11 is a diagram illustrating a visual inspection apparatus according to another embodiment of the present invention.

FIG. 11 is a diagram illustrating a visual inspection apparatus according to another embodiment of the present invention.

Referring to FIG. 11, the visual inspection apparatus according to another embodiment of the present invention can further include a light source 305 disposed above the display panel 211. Since an irregular portion can exist due to a defect of the display panel 211 and an irregular portion can also exist due to contaminants (dust or the like) 219 or scratches 214 on the display panel 211, it is necessary to distinguish between a defect of the display panel 211 itself and one due to the contaminants 219 or scratches 214. Since the contaminants 219 or the scratches 214 can reflect light in a diffused manner, unlike a defect of the display panel 211 itself, the diffused reflection can be induced by disposing the light source 305 above the visual inspection apparatus. Since the contaminants 219 or the scratches 214 have an intensity characteristic that is different from a defect of the display panel, due to the diffused reflection, the contaminants 219 or the scratches 214 can be recognized by the processor.

By vibrating the work table, the panel mounting unit and the display panel 211 on the work table can be vibrated, and such vibration further enhances the diffused reflection. In addition, by vibrating the light source 205 disposed above the display panel, it is possible to further enhance the diffused reflection. The work table can be vibrated in the vertical direction or in the horizontal direction with a vibration distance of less than the major axial length of a pixel. For example, the vibration of the work table can have a vibration distance of less than half of the minor axial length of a pixel, or a vibration distance of less than 50 μm.

The visual inspection apparatus can distinguish between irregularities due to defects of the display panel 211 and those due to other reasons such as dust 219 and scratches 214, by the use of the vibration of the light source 305 and/or the work table. Accordingly, it is possible to reduce an error wherein a normal display panel is determined to have a defective portion.

Figure 12:
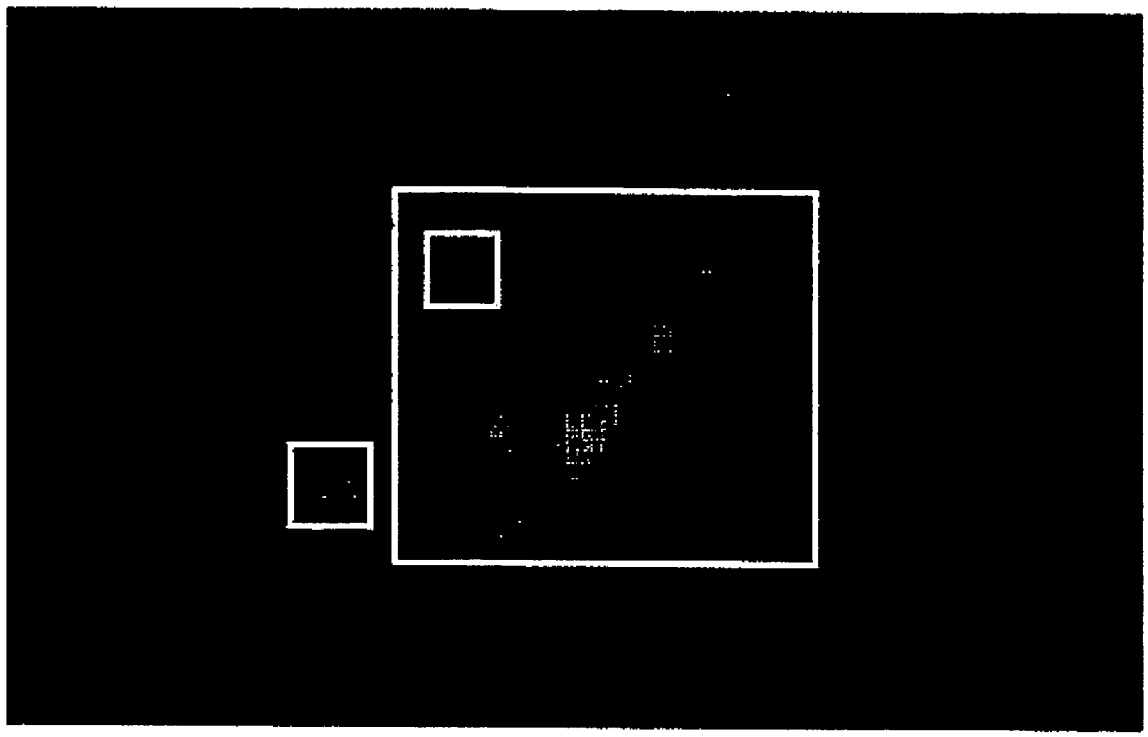
FIG. 12 is a photograph obtained by photographing a panel of which the surface is contaminated by the use of the visual inspection apparatus shown in FIG. 11.

FIG. 12 is a photograph of a display panel with a contaminated surface, taken with the visual inspection apparatus shown in FIG. 11.

Referring to FIG. 12, unlike the irregularities shown in FIG. 10, the difference in intensity due to the diffused reflection of light can be seen. The defects can therefore be distinguished on the basis of the difference in intensity.

According to the present invention described above, since the visual inspection apparatus includes the cameras arranged in a matrix, it can be used to detect a variety of irregularities of display panels of a variety of sizes. In addition, since irregularities due to defects of a display panel itself and irregularities due to other reasons (for example, dust or scratches) can be distinguished from each other, it is possible to prevent errors in which a normal display panel is determined to be defective during manufacture thereof.

What is claimed is:

1. A visual inspection apparatus comprising:
 a work table having a panel mounting unit on which a display panel is mounted;
 a camera module having a plurality of cameras that are arranged in a matrix and that photograph the display panel mounted on the panel mounting unit; and
 a processor for determining whether the display panel is defective from images of the display panel photographed with the cameras,
 wherein the plurality of cameras are arranged in a matrix with variable distances between the cameras; a second light source for irradiating light from the top side of the work table to the panel mounting unit,
 wherein one of the work table and the second light source vibrates, and
 wherein a vibration distance of the work table is smaller than the greatest length of a unit pixel in the display panel.

2. The visual inspection apparatus of claim 1, wherein a distance between the panel mounting unit and the camera module is variable.

3. The visual inspection apparatus of claim 1, further comprising:
 a first light source for irradiating light from the bottom side of the work table to the panel mounting unit; and
 an optical sheet that is disposed between the first light source and the panel mounting unit and to which a distance from the panel mounting unit is variable.

4. The visual inspection apparatus of claim 3, further comprising:
 a lower polarizing film disposed between the first light source and the optical sheet; and
 an upper polarizing film disposed between the work table and the camera module.

5. The visual inspection apparatus of claim 1, wherein the vibration distance is smaller than or equal to a half of the length of a minor axis of the unit pixel.

6. The visual inspection apparatus of claim 1, wherein the panel mounting unit is tilted by an angle of 30° to 90° about a horizontal plane, and the cameras are arranged in the direction normal to the panel mounting unit.

7. The visual inspection apparatus of claim 1, wherein the panel mounting unit further comprises a signal supply unit for supplying an image signal to the display panel.

8. A method of inspecting a display panel, the method comprising:
 mounting a display panel on a panel mounting unit of a work table;
 displaying one of a white image, a black image, a specific color image, and a middle gray-scale image on the display panel;
 photographing the display panel with a plurality of cameras arranged in a matrix while changing distances between the cameras; and
 checking for existence of a defect in the display panel from an image of the display panel photographed with the cameras, with the use of a processor wherein the photographing of the display panel with the cameras includes vibrating the work table.

9. The method of claim 8, further comprising:
 adjusting a distance between a camera module having the cameras and the panel mounting unit;
 adjusting the distances between the cameras; and
 adjusting a distance between the display panel and an optical sheet disposed below the display panel.

* * * * *